United States Patent [19]
Becker et al.

[11] Patent Number: 5,471,102
[45] Date of Patent: Nov. 28, 1995

[54] RECIPROCATING SHAFT DEVICE

[76] Inventors: Gregory R. Becker, R.R. 2 Box 182, Red Hook, N.Y. 12571; Mitchell I. Rapoport, P.O. Box 324, Woodstock, N.Y. 12498

[21] Appl. No.: 239,467
[22] Filed: May 9, 1994
[51] Int. Cl.⁶ .............................. A61M 31/00; B26F 1/24
[52] U.S. Cl. .................. 310/50; 310/17; 604/48; 604/289; 606/186
[58] Field of Search .................. 128/36; 310/47, 310/50, 51, 17; 604/22, 289, 46, 48; 606/186, 169; 81/9, 22

[56] References Cited

U.S. PATENT DOCUMENTS 3,562,566 2/1971 Kircher ............................... 310/80
4,595,850 6/1986 Woog ................................. 310/47
5,253,382 10/1993 Beny ................................. 15/22.1
5,311,633 5/1994 Herzog et al. ....................... 15/28

Primary Examiner—Thomas M. Dougherty
Assistant Examiner—Judson H. Jones

[57] ABSTRACT

A reciprocating shaft device suitable for numerous uses, including as a tattoo device, with a balanced generally symmetrical configuration having an electromagnetic coil with a shaft slidably mounted concentrically within the coil. A cylindrical housing encloses the shaft and electromagnetic coil. Damping means within the cylindrical housing quiet any noise generated by vibration. The electromagnetic coil is driven from a power source through a timer circuit and a switching circuit, the switching circuit energizing the coil with the timer circuit controlling the rate or frequency of the switching cycle.

11 Claims, 3 Drawing Sheets

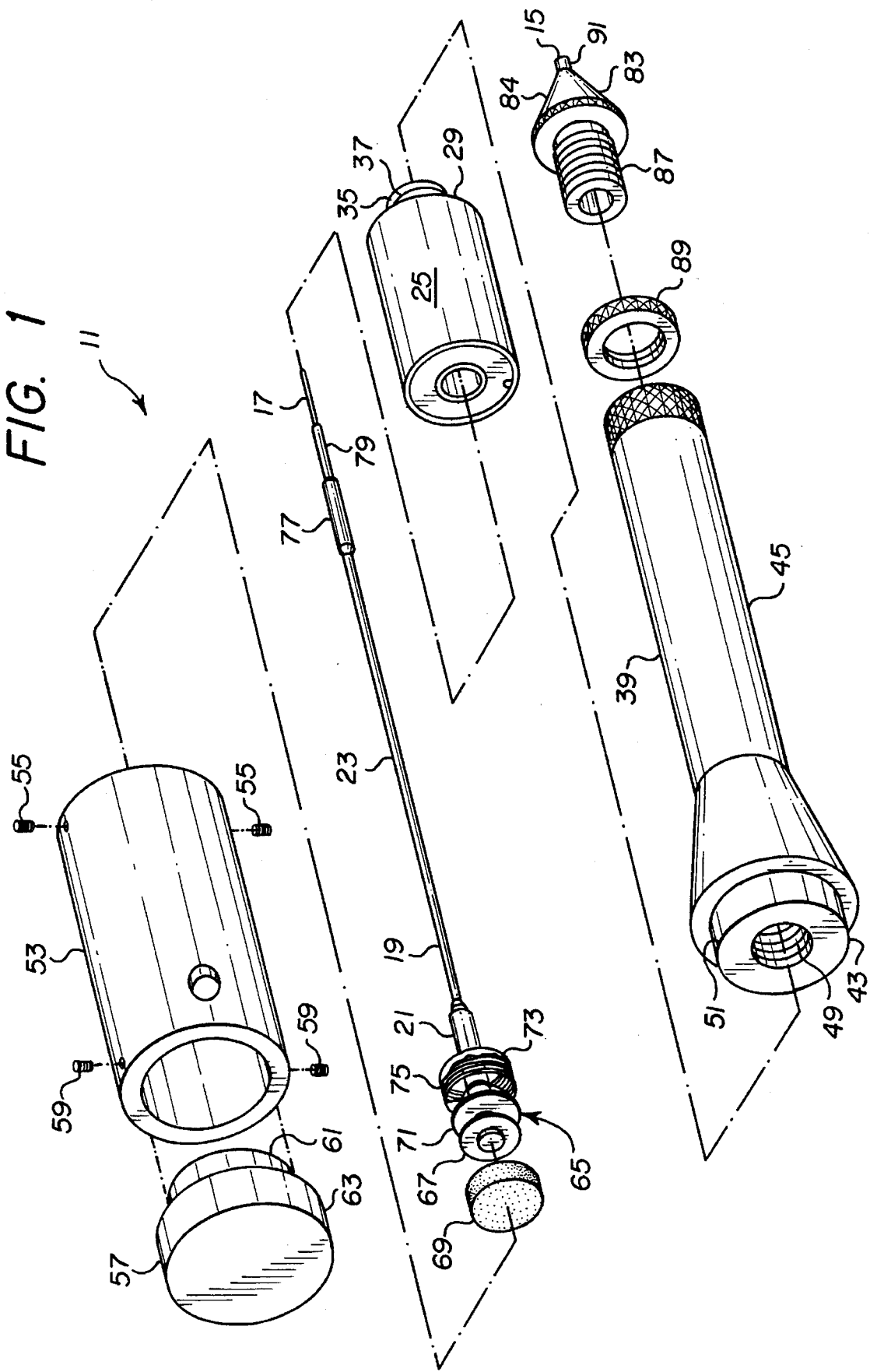

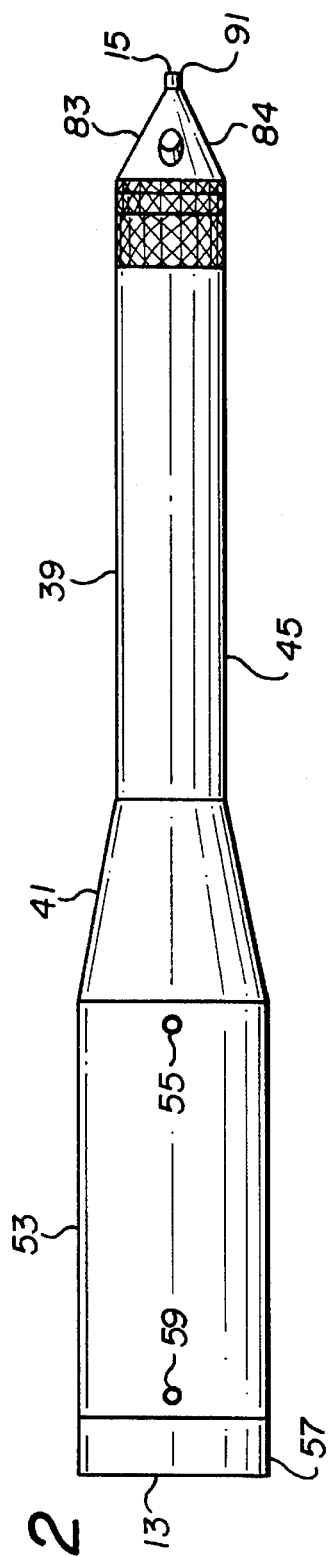
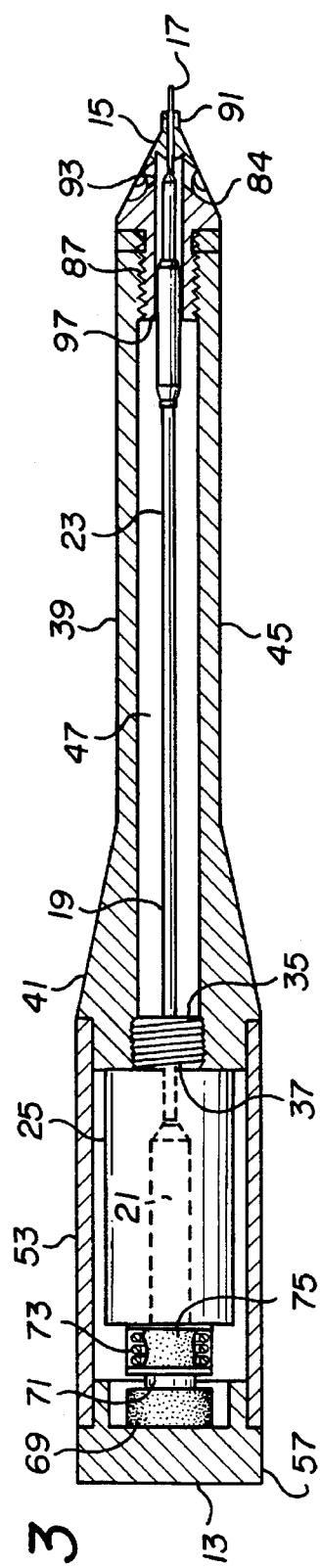
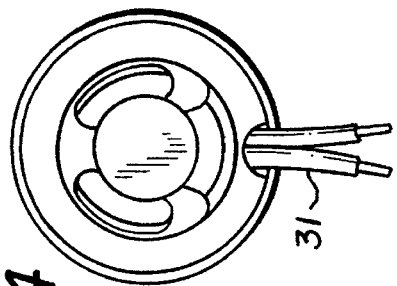

RECIPROCATING SHAFT DEVICE

BACKGROUND OF THE INVENTION

This invention relates to a reciprocating shaft device and, more specifically, to a tattoo device including such a reciprocating shaft device.

Devices having a reciprocating shaft and specifically tattoo devices are well known. Some existing units use an open, mechanical make-and-break electrical contact system which drives an electromagnetically operated pivot arm which vibrated up and down. Other versions use electric motors with eccentric cams to drive an arm up and down. The make-and-break units have visably sparking contacts and produce an extremely detrimental degree of noise when in use. Because of the sparking, such tattoo units may not be used in operating rooms or other environments where flammable or explosive gases are present. The make-and-break units also require constant adjustment due to changes in resiliency of the contact spring. Rubber bands are required to hold the needle bars in place and reduce vibration.

The motor driven designs are also noisy. Due to the limited power available in a motor of even moderately acceptable weight, the units slow down at different rates when contacting skin with different characteristics, resulting in tattoos of varying and generally poor quality.

Both designs are unbalanced as the make-and-break unit and the motor are located off center. This makes the device difficult to handle particularly when performing artistic work such as human tattooing.

Quiet operation is very important to avoid upsetting the person on whom the device is being used and when the device is being used on an animal, such as for identification purposes, the ability to use the device without upsetting the animal is most vital.

With the instant invention, the difficulties inherent in the aforementioned existing designs are overcome. The device is balanced and is similar to a large pen or pencil, thus making for easy control. The unit is so quiet that its operation is virtually undetectable. As a tattoo device, additional advantages such as eliminating splatter are provided. The instant invention is also capable of being placed in an autoclave for sterilization purposes, thus making it extremely valuable in view of the wide problem of blood transmitted diseases.

The device is readily produced, safe and quiet to operate, light in weight with superb balance providing ease in operation.

When being used as a tattoo device, the tip, in accordance with the instant invention, provides for ready discharge of tattoo fluids and the ready discharge of cleaners and disinfectants.

SUMMARY OF THE INVENTION

It is an object of this invention to provide a well balanced, quiet, light weight reciprocating shaft device and more specifically, an improved tattoo device which is easier to use and adjust, cleaner in operation, ergonomically designed, simple to clean and maintain and which produces a more precise tattoo mark than do existing designs.

It is a further object of this invention to provide a device which can be readily, sagely and properly sterilized in an autoclave to avoid potential contamination from blood borne diseases.

The device includes a shaft assembly slidably mounted at one end in an electromagnetic coil. A power supply, preferably separately located from the electromagnetic coil and shaft, includes a power source and a switching circuit and a timer circuit. The switching circuit controls the flow of electrical power to the electromagnetic coil by turning the electrical power on and off. The timer circuit controls the rate or frequency and duration (meaning the length of a pulse) of the switching cycle.

A coil assembly is provided with an electromagnetic coil encased within an inner housing. A connecting means, smaller in diameter than the inner housing, extends from the inner housing. A coil cover, which is cylindrical, encases the coil assembly. The coil cover is secured to the nose assembly, which is also cylindrical, and which encases the shaft assembly within a passageway concentrically located through the nose assembly. The nose assembly is secured to the inner housing by means of the connecting means. A cartridge holder may be located at the end of the shaft assembly which, if used as a tattoo device, would be used to hold a needle assembly which includes a needle cartridge and at least one needle.

A tip is affixed, preferably by a threaded section, to the end of the nose assembly. The tip is preferably generally conically shaped being reduced to a minimum diameter at its distal end. A passageway is also concentrically located through the tip and is aligned with the passageway through the nose assembly. The passageway through the tip assembly reduces in size near the distal end of the tip assembly. At the point where the passageway reduces in size a groove of reduced size is cut around the opening of the passageway. Approximately midway in the conical section of the tip, at least one opening is formed from the exterior of the passageway to permit the introduction of tattoo fluid and cleaners.

At the end of the coil cover, a cap is located which can be threaded into the coil cover, press fitted into the coil cover or secured by a locking screw. The shaft assembly within the electromagnetic coil has a substantially larger diameter than the portion of the shaft assembly which extends through the nose assembly and tip assembly. The end of the shaft extends beyond the electromagnetic coil toward the cap, but within the coil cover. Spring and dampening means are provided between the cap and the inner housing.

DESCRIPTION OF THE DRAWINGS

FIG. 1 is an exploded pictorial view of the reciprocating shaft device including the cartridge holder and cartridge with needles such as would be included when the device is used as a tattoo device.

FIG. 2 is a side view of the device showing the hole through the tip.

FIG. 3 is a longitudinal cross-sectional view showing the inner housing and the shaft assembly with the needle cartridge and cartridge with a needle.

FIG. 4 is a view of the upper end of the reciprocating shaft device with the cap removed, showing the end of the shaft assembly.

FIG. 5 is an enlarged cross-sectional view of the lower end of the reciprocating shaft device showing the holes through the tip for the introduction of fluids and showing the point of reduction.

DESCRIPTION OF THE PREFERRED EMBODIMENT

Figure 6:
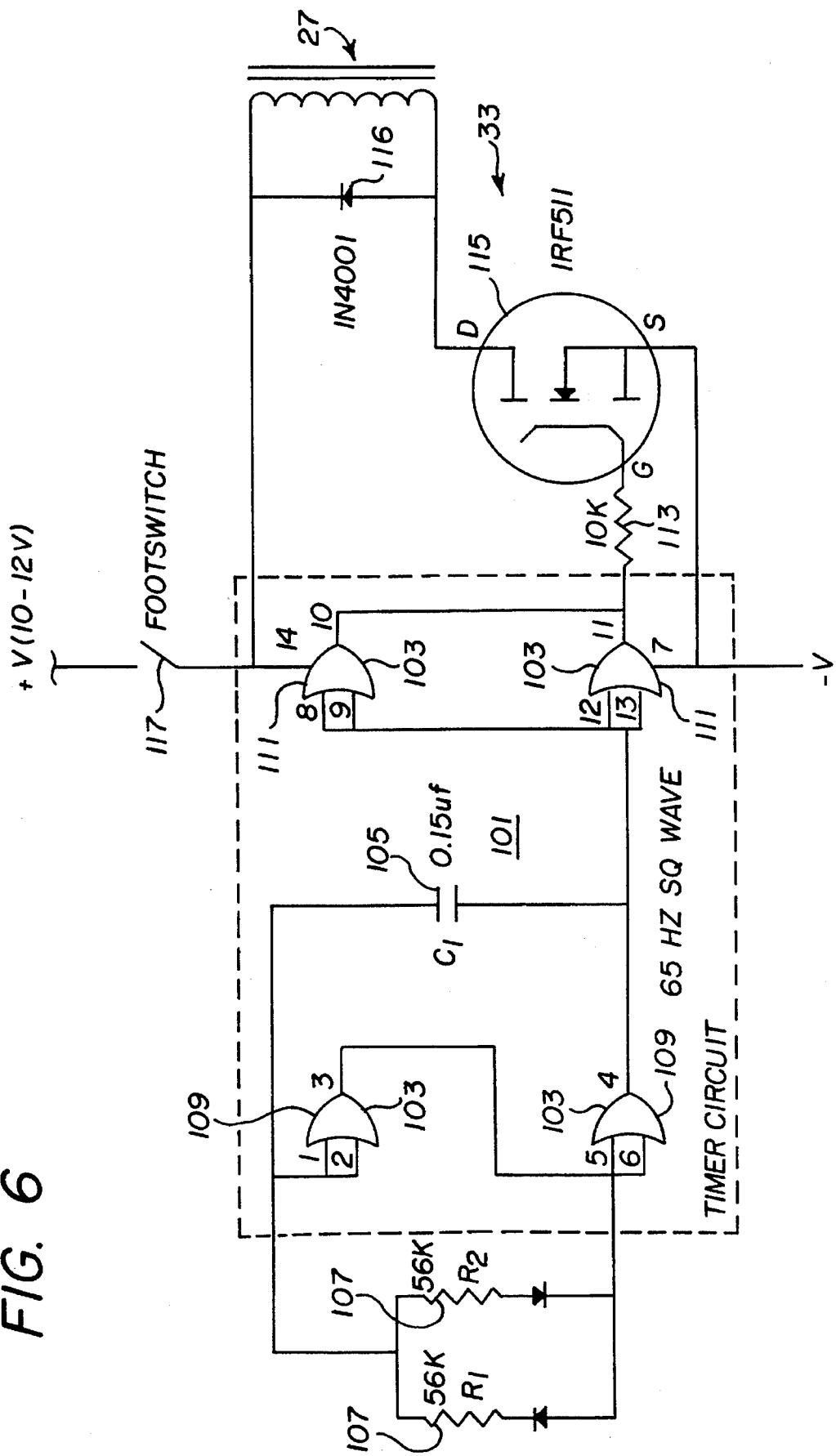
FIG. 6 is a schematic view of the electrical circuit.

Referring now to FIG. 1, a reciprocating shaft device 11 is shown. The reciprocating shaft device 11 has an upper end 13 and a lower end 15. The lower end 15 is where the reciprocating shaft device 11 is applied to a workpiece, as for example, when used as a tattoo device, when a tattoo needle 17 is applied to the skin of the recipient (not shown). The upper end 13 is the opposite end from the lower end 15.

Concentrically within the reciprocating shaft device 11 is a shaft assembly 19 which has a circular cross section. The shaft assembly 19 has two sections, namely an upper section 21, and a lower section 23. The upper section 21 is located toward the upper end 13 of the reciprocating shaft device 11 and the upper section 21 is larger in diameter than the lower section 23 located toward the lower end 15 of the reciprocating shaft device 11. The lower section 23 of the shaft assembly 19 is also substantially longer than the upper section 21 of the shaft assembly 19 and is reduced in diameter being, in general, a rod.

A coil assembly 25 is mounted symetrically about the shaft assembly 19 toward the upper end 13 of the reciprocating shaft device 11. The coil assembly 25 includes an electromagnetic coil 27 located within an inner housing 29. The electromagnetic coil 27 encases nearly all of the upper section 21 of the shaft assembly 19 and a small part of the lower section 23 of the shaft assembly 19 adjacent to the upper section 21. The end of the shaft assembly 19 located toward the upper end 13 extends beyond the inner housing 29. Electrical leads 31 enter the inner housing 29 to supply electrical power from an electrical supply 33 to the electromagnetic coil 27. The electrical supply 33, to be subsequently described, is preferably separate from the electromagnetic coil 27.

A connecting means 35 extends from the lower end 15 of the inner housing 29. The connecting means 35 is of smaller diameter than the inner housing 29 and preferably includes an outer thread 37, but the thread could be eliminated and other means such as a press fit or a locking screw (not shown) could be used in place of the outer thread 37.

A nose assembly 39, best shown in FIG. 5, has a conical section 41 located toward the upper end 13. A coupling means 43 extends from the nose assembly 39 located toward the upper end 13. The nose assembly 39 tapers down to an elongated cylindrical section 45 which extends from the conical section 41 toward the lower end 15. A passageway 47 which is generally concentric extends through the nose assembly 39. The coupling means 43 has an internal thread 49. The outer or external thread 37 of the connecting means 35 which extends from the inner housing 29 is threaded into the internal thread 49 of the nose assembly 39, unless another means other than the two threads 37, 49 is used. As a result, the nose assembly 39 extends from the inner housing 29 of the coil assembly 25.

The external surface 51 of the coupling means 43 of the nose assembly 39 has a diameter slightly larger than the diameter of the inner housing 29. A coil cover 53 is mounted on the external surface 51 of the coupling means 43, over and generally symetrically around the inner housing 29 of the coil assembly 25. The coil cover 53 is a cylindrical member. The inner diameter of the coil cover 53 mates with the exterior diameter of the coupling means 43, which is also cylindrical. Although a thread (not shown) can be used for mounting the coil cover 53 on the coupling means 43, it is preferred to use a close fit with locking screw 55 so that the coil cover 53 is mounted around the inner housing 29 and rigidly secured to the coupling means 43 of the nose assembly 39. The coil cover 53 is longer than the inner housing 29 and, therefore, extends beyond both the inner housing 29 and the upper section 21 of the shaft assembly 19 toward the upper end 13;

A cap assembly 57 is provided which may be threaded, but is preferably pressed or secured with locking screw 59 fitted to the end of the coil cover 53. The cap assembly 57 has a cylindrical section 61 to mate with the interior of the coil cover 53 and an outer crown 63 for being readily gripped by the hand of an operator.

A dampening means 65 is provided within the coil cover 53 between the cap assembly 57 and the upper end 13 of the shaft assembly 19 to absorb the vibration of the shaft assembly 19 toward the upper end 13 and between the end of the shaft assembly 19 and the inner 29 which is slidably mounted in the electromagnetic coil 27. Various means of dampening are possible, but a C-clip 67 located at the end of the shaft assembly 19 toward the upper end 13 with a foam washer 69 against it, and a foam and/or plastic washer 71 against the cap assembly 57 provides one possible version of a dampening means 65. A coil spring 73 inside a foam disk 75 may also be preferably located between the inner housing 29 and the end of the shaft assembly 19 which serves as both a spring and a dampener. Other combinations of dampening and resilience may be provided.

Particularly, if the shaft assembly 19 is used for tattooing, the end of the shaft assembly 19 toward the lower end 15 includes a cartridge holder 77 affixed to the end of the shaft assembly 19 toward the lower end 15. A cartridge 79 with one or more tattoo needles 17 may be fitted into and held by the cartridge holder 77.

At the end of the nose assembly 39 toward the lower end 15, a tip 83 is placed. The tip 83 has a conical section 84 with a passageway 85 through it which aligns with the passageway 47 of the nose assembly 39. The end of the tip 83 toward the upper end 13 includes a cylindrical section 87 which has a diameter having a size between the larger and smaller diameters of the conical section 84 of the tip 83. The cylindrical section 87 of the tip 83 is preferably threaded. A locking nut 89 is mounted on the cylindrical section 87 of the tip 83. Since the conical section 84 of the tip 83 is the major portion of the tip, it forms a configuration similar to the end of a sharpened pencil and includes a short section 91 which is cylindrical and which is located toward the lower end 15. The passageway 85 through the cylindrical section 87 of the tip 83, and for a substantial part of the conical section 84 of the tip 83, is similar in size to that of the passageway 47 through the nose assembly 39. The passageway 85 adjacent the lower end 15 of the tip 83 abruptly reduces in size forming a reduced passageway 93. A groove 95 is located about the reduced passageway 93 at the point of reduction 97.

The cylindrical section 87 of the tip 83 is secured to the nose assembly 39 preferably by a thread. The extent that the tip 83 extends from the nose assembly 39 is adjusted by use of the locking nut 89 which is tightened down against the nose assembly 39. If used as a tattoo device, the needles 81 reciprocate in and out of the tip 83 at the lower end 15.

When the reciprocating shaft device 11 is used as a tattooing device, a hole 99 is provided in the tip 83, which hole 99 is primarily used for the introduction of cleaning and sterilization fluids to clean the tip 83 and the tattoo needles 17. When the reciprocating shaft device 11 is operating and the tip 83 is dipped in tattooing fluids, said fluids are drawn into the passageway 85 and accumulate in the groove 95. The groove 95 therefore serves as a reservoir for tattooing fluid.

The coil assembly 25, and in particular the electromagnetic coil 27, is repeatedly energized at a variably selectable rate so as to cause the shaft assembly 19 to reciprocate. The dampening means 65 serves to reduce vibration to such a minor level that operation of the reciprocating shaft device 11 is virtually undetectable from sound or mechanical vibration. The electromagnetic coil 27 is actuated by an electronic circuit, best shown in FIG. 6, which includes primarily a quad NOR gate circuit 101 within one intergrated chip. The quad NOR gate circuit 101 includes four gates 103. Two of the gates 103 and a capacitor 105 form a timer circuit 106. Two resistors 107 are located in parallel with two gates 109 which are part of the timer circuit 106, each of the two resistors 107 being connected parallel with one another. The two resistors 107 in combination with the capacitor 105 set the pulse rate. The other two gates 111 serve as a buffer to the timer circuit 106.

A buffer resistor 113 is located in series with a Metal Oxide Semiconducting Field Effect Transitor (MOSFET) 115 which switches the current to the electromagnetic coil 27 based upon the pulses generated by the timer circuit 106. In parallel with the electromagnetic coil, there is a diode 116 which shunts and dampens the voltage spike caused by the electromagnetic coil 27 turning on and off. Electrical power is supplied by a power source and is controlled through a switch 117, preferably a foot switch if the reciprocating shaft device 11 is used as a tattoo device.

By means of the circuit and the electromagnetic coil, the shaft assembly 19 rapidly reciprocates back and forth at an interval which may be used for many purposes, but in particular for tattooing. The operation of the reciprocating shaft device 11 is virtually without sound and mechanical vibration because the vibration is minimized by design and effectively dampened. The reciprocating shaft device 11 is ergonomically balanced and can be held in the hand of an operator as would be a large pencil or pen.

The invention may be embodied in other specific forms without departing from the spirit or essential characteristics thereof. The present embodiments are, therefore, to be considered in all aspects as illustrative and not restrictive. The scope of the invention is indicated by the appending claims rather than the foregoing description and all changes which come within the meaning and range of equivalency of the claims are, therfore, intended to be embraced therein.

We claim:

1. A reciprocating shaft device having an upper end and a lower end, said reciprocating shaft device comprising:

a shaft assembly;

an inner housing;

a coil assembly including an electromagnetic coil, the electromagnetic coil being encased within the inner housing;

a nose assembly secured to the coil assembly and having a passageway extending longitudinally and generally concentrically through it, the shaft assembly extending into the passageway of the nose assembly and being generally symmetrically located and slideably mounted within the magnetic coil;

a coil cover affixed to the nose assembly and encasing the inner housing;

a cap assembly secured to the coil cover assembly at the upper end;

dampening means located at the end of the shaft assembly;

an electrical circuit means repeatedly to energize the electromagnetic coil at a variable selectable rate so as to cause the shaft assembly to reciprocate.

2. A reciprocating shaft device according to claim 1 wherein the shaft assembly includes an elongated member with two sections, an upper section located toward the upper end and a lower section located toward the lower end, the upper section having a diameter greater then the lower section and the lower section being longer than the upper section.

3. A reciprocating shaft device according to claim 1 wherein:

the shaft assembly includes an elongated member with two sections, an upper section located toward the upper end and a lower section located toward the lower end.

4. A reciprocating shaft device having an upper end and a lower end, said reciprocating shaft device comprising:

a shaft assembly including an elongated member with two sections, an upper section located toward the upper end and a lower section located toward the lower end, the upper section having a diameter greater then the lower section and the lower section being longer than the upper section;

a coil assembly including an electromagnetic coil;

an electromagnetic coil being encased within the inner housing;

a nose assembly secured to the coil assembly and having a passageway extending longitudinally and generally concentrically through it, the shaft assembly extending into the passageway of the nose assembly;

a coil cover assembly affixed to the nose assembly and encasing the inner housing;

a cap secured to the coil cover assembly at the upper end;

dampening means located at the end of the shaft assembly;

an electrical circuit means to repeatedly energize the electromagnetic coil at a variable selectable rate so as to cause the shaft assembly to reciprocate.

5. A reciprocating shaft device according to claim 1 wherein:

the shaft assembly includes an elongated member with two sections, an upper section located toward the upper end and a lower section located toward the lower end, and the nose assembly includes a conical section located toward the upper end and a cylindrical section which extends from the conical section, the cylindrical section being substantially longer than the conical section.

6. A reciprocating shaft device according to claim 1 wherein:

the nose assembly includes a conical section located toward the upper end and a cylindrical section which extends from the conical section, the cylindrical section being substantially longer than the conical section, said reciprocating device further including a tip assembly affixed to the cylindrical section of the nose assembly.

7. A reciprocating shaft device having an upper end and a lower end, said reciprocating shaft device comprising: a shaft assembly including an elongated member with two sections, an upper section located toward the upper end and a lower section located toward the lower end, the upper section having a diameter greater then the lower section and the lower section being longer than the upper section;

a coil assembly including an electromagnetic coil within the inner housing, the electromagnetic coil encasing almost all of the upper section of the shaft assembly, and a small portion of the lower section of the shaft assembly, the shaft assembly being symmetrically and slideably mounted within the electromagnetic coil, the inner housing having a connecting means located toward the lower end;

the nose assembly including a conical section located toward the upper end and a cylindrical section which extending from the conical section, the cylindrical section being substantially longer than the conical section, a coupling means extending from the conical section toward the upper end, the coupling means being affixed to the connecting means of the inner housing, the nose assembly having a passageway extending longitudinally through the nose assembly, the passageway being generally concentrically located in the nose assembly;

a coil cover including a cylindrical sleeve engaging and secured to the coupling, means of the nose assembly and encasing the inner housing and extending beyond both the inner housing and the shaft assembly toward the upper end;

a tip assembly including a conical member with a threaded extension at the upper end, said tip assembly having a passageway generally concentrically located longitudinally through the tip assembly, said passageway through the tip assembly being generally aligned with the passageway through the nose assembly;

a cap secured to the coil cover;

dampening means located at the end of the shaft assembly;

an electrical circuit means to repeatedly energize the electromagnetic coil at a variably selectable rate so as to cause the shaft assembly to reciprocate.

8. A reciprocating shaft device according to claim 7 wherein the electrical circuit means including a NOR gate with four gates, two of which with a capacitor and a pair of resistors form a timer circuit and another two of which together with a buffer resistor and a MOSFET form a switch which is controlled by the timer circuit in series with the electromagnetic coil.

9. A reciprocating shaft device having an upper end and a lower end, said reciprocating shaft device comprising:

a shaft assembly including an elongated member with two sections, an upper section located toward the upper end and a lower section located toward the lower end, the upper section having a diameter greater then the lower section and the lower section being longer than the upper section;

a coil assembly including an electromagnetic coil within the inner housing, the electromagnetic coil encasing almost all of the upper section of the shaft assembly, and a small portion of the lower section of the shaft assembly, the shaft assembly being symmetrically and slideably mounted within the electromagnetic coil, the inner housing having a connecting means located toward the lower end, the connecting means having a diameter smaller than the diameter of the inner housing and the connecting means having an internal thread, the shaft assembly extending beyond the inner housing toward the upper end, substantially longer then the conical section, a coupling means extending from the conical section toward the upper end, the coupling means being affixed to the connecting means of the inner housing, the nose assembly having a passageway extending longitudinally through the nose assembly, the passageway being generally concentrically located in the nose assembly;

a coil cover including a cylindrical sleeve engaging and secured to the coupling, means of the nose assembly and encasing the inner housing and extending beyond both the inner housing and the shaft assembly toward the upper end;

a tip assembly including a conical member with a threaded extension at the upper end, said tip assembly having a passageway generally concentrically located longitudinally through the tip assembly, said passageway through the tip assembly being generally aligned with the passageway through the nose assembly; the passageway through the tip assembly being reduced in size adjacent the lower end, a groove being formed in the tip assembly about the upper end of the passageway which is reduced in size, an opening being located through the tip assembly to the passageway at generally a right angle to the passageway, the threaded extension of the tip assembly engaging the lower end of the nose assembly, a locking nut mounted on the threaded extension to adjust the position of the tip assembly in relation to the nose assembly;

a cap assembly to the coil cover assembly at the upper end;

dampening means between the cap assembly and the end of the shaft assembly and between the end of the shaft assembly and the inner housing; and an electrical circuit means repeatedly to energize the electromagnetic coil at a variably selectable rate as to cause the shaft assembly to reciprocate.

10. A reciprocating shaft device according to claim 9 further including a holding means affixed to the shaft assembly adjacent to the lower end, the holding means including a hollow cylinder with a plurality of slots extending longitudinally along the cylinder.

11. A reciprocating shaft device according to claim 9 wherein the electrical circuit means includes a NOR gate circuit with four gates, two of which with a capacitor and a pair of resistors form a timer circuit and two of which, together with a buffer resistor and a MOSFET form a switch, which is controlled by the timer circuit in series with a electromagnetic coil.

\* \* \* \* \*